United States Patent [19]
Affeld

[11] Patent Number: 5,346,458
[45] Date of Patent: Sep. 13, 1994

[54] ELECTROHYDRAULIC ENERGY CONVERTER FOR CARDIAC ASSIST DEVICES AND ARTIFICIAL HEARTS

[76] Inventor: Klaus Affeld, Niebuhrstr. 11A, 1 Berlin 12, Fed. Rep. of Germany

[21] Appl. No.: 720,322

[22] Filed: Jun. 25, 1991

[30] Foreign Application Priority Data

Jun. 25, 1990 [DE] Fed. Rep. of Germany ....... 4020120

[51] Int. Cl.$^5$ ............................................. A61N 1/362
[52] U.S. Cl. ............................................. 600/16; 623/3
[58] Field of Search ................................. 600/16–18; 623/3

[56] References Cited

U.S. PATENT DOCUMENTS

| | | |
|---|---|---|
| 4,173,796 | 11/1979 | Jarvik . |
| 4,382,199 | 5/1983 | Isaacson . |
| 4,453,537 | 6/1984 | Spitzer . |
| 4,888,011 | 12/1989 | Kung et al. . |
| 5,006,104 | 4/1991 | Smith et al. .................. 600/16 |
| 5,041,132 | 8/1991 | Miyata ........................... 623/3 |

FOREIGN PATENT DOCUMENTS

| | | |
|---|---|---|
| 1528798 | 9/1969 | Fed. Rep. of Germany . |
| 2107000 | 8/1972 | Fed. Rep. of Germany . |
| 0239723 | 10/1986 | Fed. Rep. of Germany ........ 600/16 |
| 143798 | 2/1931 | Switzerland . |

OTHER PUBLICATIONS

G. Geisselbrecht et al., "An Implantable Driving System for Left Ventricular Assist Blood Pumps", *Biomedizinische Technik*, Bd. 19, No. 6 1974, Berlin, pp. 217–224.

*Primary Examiner*—Lee S. Cohen
*Assistant Examiner*—John P. Lacyk
*Attorney, Agent, or Firm*—Robert J. Koch

[57] ABSTRACT

An apparatus for converting electric energy into pumping energy is disclosed. The apparatus is utilized to drive a cardiac assist device or an artificial heart. These devices are volume displacement blood pumps which require an alternating force or pressure for their pumping action. To generate this alternating pressure, a centrifugal pump driven by an electric motor pumps a hydraulic fluid which acts on the diaphragm of a blood pump. The alternating flow of the hydraulic transmitting fluid is generated by an axial shift of the impeller of the centrifugal pump.

18 Claims, 3 Drawing Sheets

ELECTROHYDRAULIC ENERGY CONVERTER FOR CARDIAC ASSIST DEVICES AND ARTIFICIAL HEARTS

BACKGROUND OF THE INVENTION

In the last years the application of an artificial heart has become a clinical practice. Most of the blood pumps which are implanted into the body are driven by air, the pressurized air is delivered by a driving system located outside of the body. The pneumatic tubes leading to the blood pumps penetrate the skin and often lead to infections. Moreover, the driving systems are clumsy and limit the activity of the patient. These disadvantages pose severe limitations to the therapeutic value of such a pneumatic artificial heart or cardiac assist system. A possible solution to these problems is a totally implantable system. The energy can be transmitted into the body according to the transformer principle, one coil being implanted under the skin of the patient, the other being energized by a battery and placed close to the skin outside the body. The electric energy brought into the body in this manner then has to be converted into mechanical energy. A brushless electric motor is one of the proven ways to perform this task. However, the rotary energy of the motor has to be converted into a displacement of the walls of the blood pump, usually made of a flexible and blood compatible material. Mechanical systems have been designed which make use of a cam or a rollerscrew. It has been shown that these systems can work safely over an extended period of time, but still there is a general agreement, that minimizing the number of movable parts improves the inherent safety of such an energy converter. Attempts to move in this direction have been made with electrohydraulic systems. One system utilizes an axial flow pump, which consists of an impeller directly attached to the rotor of an electric motor. The impeller moves a transmitter fluid, the latter acting on the diaphragms of the blood pumps. The blood pumps require an alternating flow of the transmitter fluid, which is achieved by means of reversing the motor of the axial flow pump. This device has only one moving part and should have a great potential for safety. In practice, however, the simplicity is lost because the reversing action of the motor forbids the use of hydrodynamic bearings and requires ball bearings. Thus, in fact, more parts are introduced and those ball bearings pose a problem because of their limited durability. Another electrohydraulic energy converter makes use of a continuously running radial flow centrifugal pump. The alternating flow required by the blood pumps is generated with the help of a sleeve valve. So another element was introduced.

It is apparent to one skilled in the science of engineering that the prior art in the field has not successfully solved the problem of the energy conversion. The systems that have become known or partially have been applied in the clinical practice have severe disadvantages, mainly that the safety is not optimal. Obviously, if only one moving part could perform the desired task, the inherent safety would be greater than in the systems presently known. Safety of the system finally is the most important quality for the patient, who is physically and, as a human being, psychologically depending on the proper and safe functioning of the system.

SUMMARY OF THE INVENTION

It is an object of the present invention to provide an apparatus for converting electric energy into pumping energy which has the greatest inherent safety possible, because the apparatus has only a single moving part.

A preferred embodiment of the present invention is disclosed in connection with reference to the figures in which:

DETAILED DESCRIPTION OF THE PREFERRED EMBODIMENT

Figure 1:
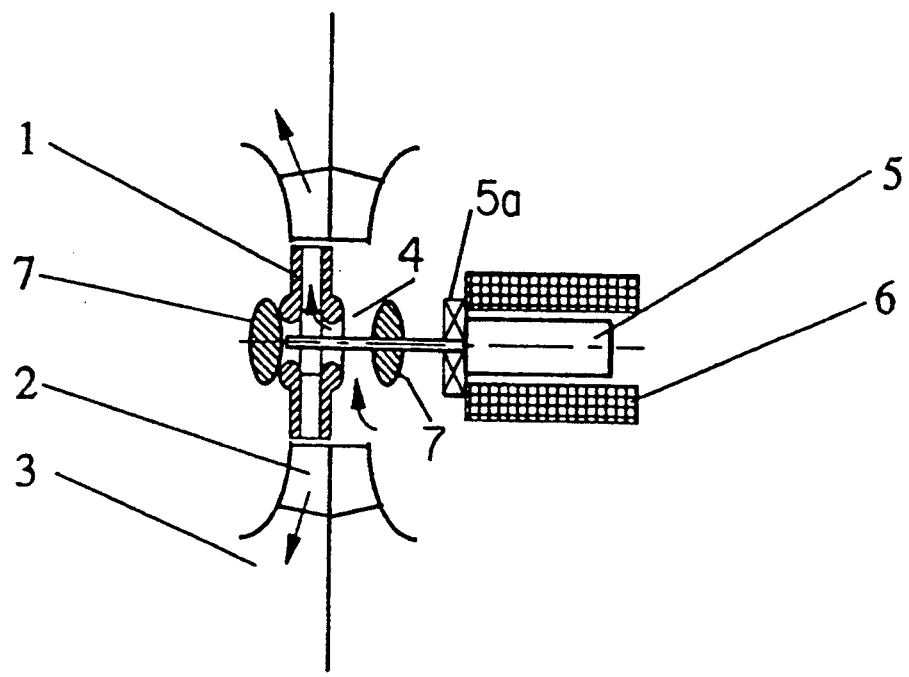
FIG. 1 is a simplified longitudinal section through an energy converter.

FIG. 1 is a simplified longitudinal section through an energy converter. The impeller 1 feeds into the diffusor 2 and then into the chamber 3 to act upon the diaphragm of the blood pump, which is not shown in this figure. The flow of the transmitter fluid enters the impeller through the inlet 4. The impeller 1 is connected to the rotor 5, which turns in the stator 6, and is supported by rotor bearing 5a. The rotor bearing may permit rotational and axial movement of the rotor and the impeller. The rotor bearing may also be configured as a rotor-impeller bearing element. The occluders 7 are fixed in relation to the diffusor and occlude either inlet of the impeller 1.

Figure 2:
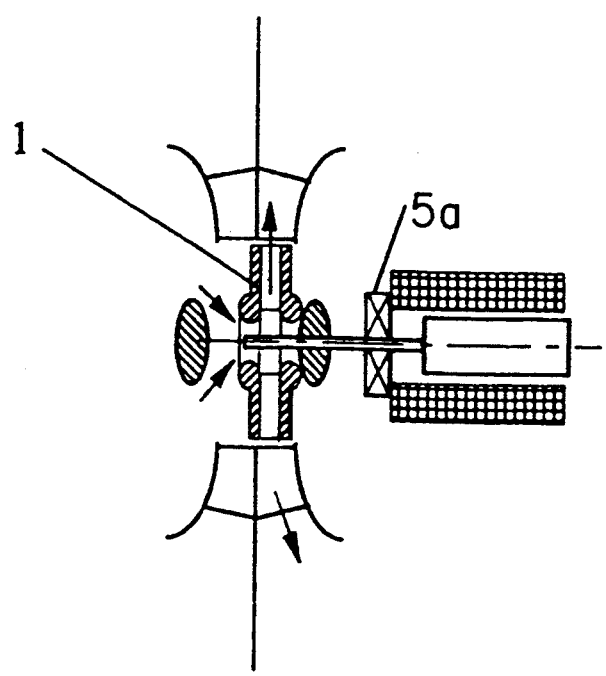
FIG. 2 is a simplified longitudinal section through the same energy converter.

FIG. 2 is a simplified longitudinal section through the same energy converter, but here the impeller 1 is shifted axially and now feeds into another diffusor. The flow now enters through the other inlet. The previous inlet on the other side of the impeller now is blocked by the other occluder. In this manner the impeller reverses the flow with the only requirement of an axial shift.

Figure 3:
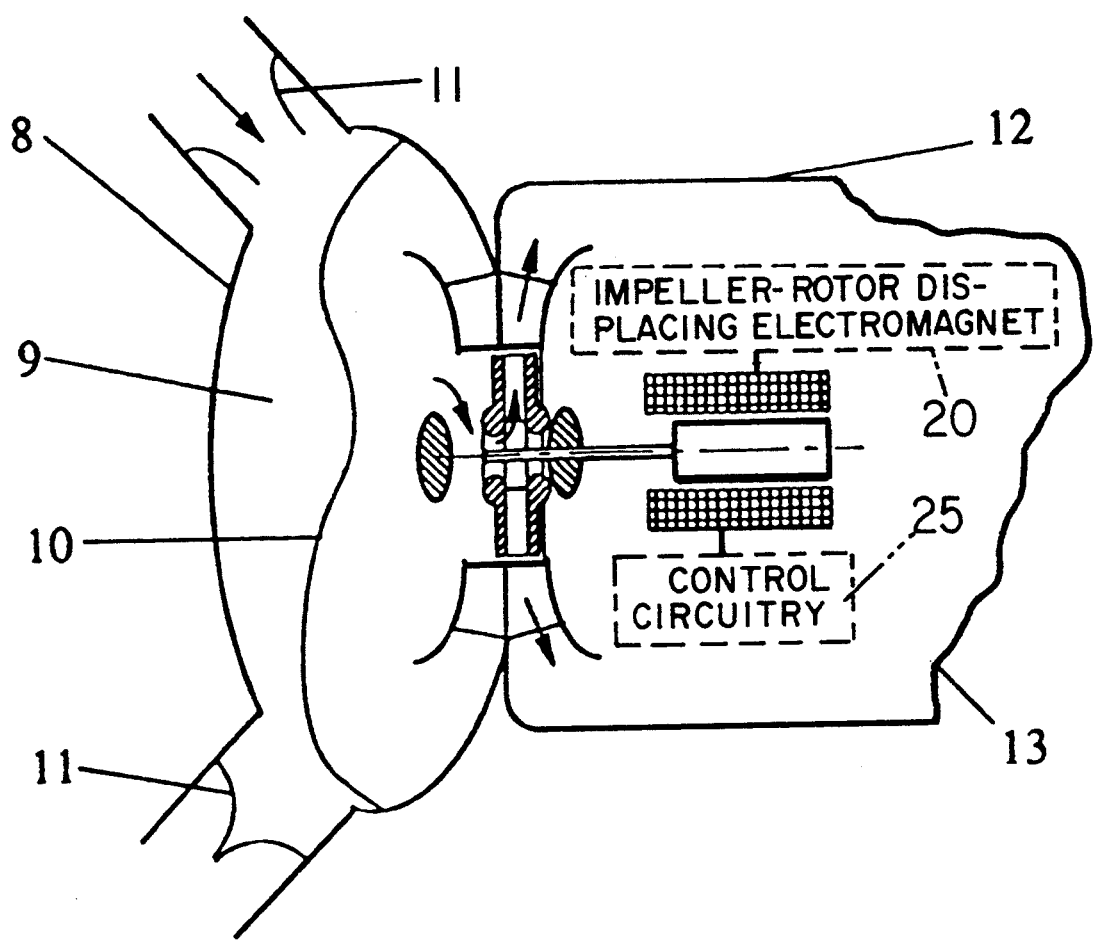
FIG. 3 is a simplified longitudinal section through the energy converter shown in arrangement with a blood pump.

FIG. 3 is a simplified longitudinal section through the energy converter shown in arrangement with a blood pump. The housing 8 contains the blood 9, which is separated from the transmitter fluid by the diaphragm 10. Two passive valves 11 control the direction of the blood flow through the blood pump. The energy converter is contained in a rigid housing 12, which at one side has a flexible wall 13 which acts as a displacement chamber. In the case of a total artificial heart this flexible wall 13 would be a diaphragm of the second blood pump, since a total artificial heart requires two ventricles.

According to the embodiment of the invention shown in FIGS. 1–3, the electric field generated in stator 6 permanently acts on rotor 5 and keeps the rotor in constant unidirectional rotation. The impeller-rotor unit may be displaced by any conventional displacing mechanism 10. The impeller-rotor unit may also be axially displaced by an electromagnet. However, for the purposes of clarity, this magnet is not shown.

Figure 4:
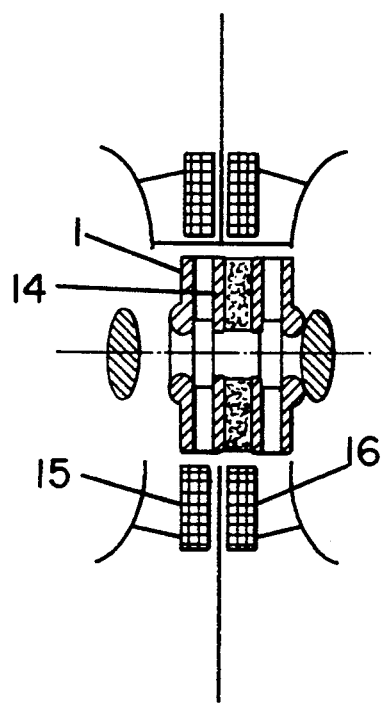
FIG. 4 is a simplified longitudinal section through an energy converter with the brushless electric motor fully integrated.

FIG. 4 is a simplified longitudinal section through an energy converter with the brushless electric motor fully integrated. The impeller 1 contains magnets which form the rotor 14. There are two stators 15 and 16 to drive the impeller 1. Only one of the stators is active at a time. The electric field also actuates the axial shift in order to reverse the flow. The bearings may be arranged in a variety of ways according to the known state of the art.

Figure 5:
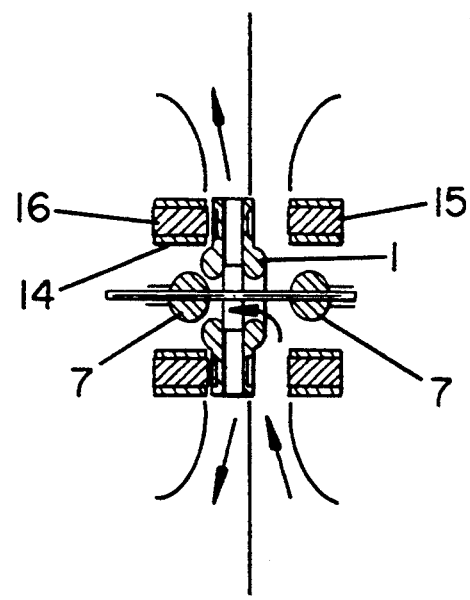
FIG. 5 is a simplified longitudinal section through still another form of the energy converter.

FIG. 5 is a simplified longitudinal section through still another form of the energy converter. In this case the magnets 14 are integrated in the faces of the impeller. The stators 15 and 16 are arranged sidewise. Again, as in the arrangement as shown in FIG. 5, the driving electric field also actuates the axial shift.

For the embodiments of the invention shown in FIGS. 4 and 5, the control circuitry 25 (see FIG. 3) for the displacement of the impeller may be an integral part of the electronics which drive the motor. The activation of stator 16 turns the rotor and the impeller, while keeping the impeller in place. Once stator 15 is activated, stator 16 is idle. The electromagnetic forces which drive the rotor at the same time displace the impeller to its new position and with that action, the transmitter fluid flow of the blood pump reverses.

The displacement of the impeller and the accompanying reversal of the transmitter fluid flow is initiated when the diaphragm of the blood pump reaches one of its two end positions, which may be the endsystolic or the endiastolic position. The diaphragm position may be sensed by a magnet attached to the diaphragm and an associated hall effect sensor or by other conventional mechanisms, such as optical sensors.

Another way of initiating the displacement of the impeller is switching from one stator to the other by a fixed rate.

The preferred embodiment of the present invention combines a continuously running radial centrifugal pump with a brushless electric motor combined with a special housing and an arrangement of electromagnets to provide an axial shift of the impeller-rotor unit to generate an alternating flow while a constant rotation of the impeller is maintained. The alternating flow of the transmitter fluid is required for the actuation of displacement blood pumps. Also, it is possible to generate a constant hydrodynamic film and avoid mechanically contacting surfaces, meaning that the lifetime of the energy converter is virtually unlimited. This is an aspect which definitely increases the safety of the device and contributes to the well being of the patient. An additional advantage of the proposed invention is that the motor rotation is not reversed. Therefore, a very smooth pumping action is achieved, which immediately is sensed by the patient and provides a feeling of security required for normal life.

I claim:

1. A system to convert electric energy into hydraulic energy of a transmitter fluid to actuate and control a diaphragm or flexible wall of a blood pump for use in a cardiac assist system or in a total artificial heart comprising:
   a continuously running radial centrifugal hydraulic pump with an impeller having inlets on both sides;
   first and second diffusor elements arranged back to back, said first diffusor element connected to and issuing into a housing of a first blood pump, and said second diffusor element connected to and issuing into either a displacement chamber, or a housing of a second blood pump, wherein said first and second diffusor elements circumferentially surround said impeller;
   a brushless electric motor mounted in fixed relationship to said first blood pump housing and having a stator and a rotor, said rotor being connected with the impeller of the centrifugal pump; and
   means for initiating axial movement of said rotor and said impeller.

2. A system to convert electric energy into hydraulic energy as defined in claim 1, in which an occluder blocks the inlet of the impeller of either side depending on its axial position.

3. A system to convert electric energy into hydraulic energy as defined in claim 1, in which the rotor of the motor is an integrated part of the impeller.

4. A system to convert electric energy into hydraulic energy as defined in claim 1, wherein an axial shift of said rotor and said impeller is actuated by a driving electromagnetic field.

5. A system to convert electric energy into hydraulic energy as defined in claim 1, wherein an axial shift of said rotor and said impeller and holding in position is done by the action of magnets.

6. A system to convert electric energy into hydraulic energy as defined in claim 1, further comprising:
   a rotor bearing supporting said rotor and configured so said rotor and said impeller move in at least an axial direction.

7. A diaphragm or flexible wall blood pump comprising:
   a continuously running radial centrifugal hydraulic pump with an impeller having inlets on both sides;
   two diffusor elements arranged back to back, one connected to and issuing into a blood pump housing and the other connected to and issuing into a displacement chamber, wherein said diffusor elements circumferentially surround said impeller;
   a brushless electric motor mounted in fixed relationship to said blood pump housing and having a stator and a rotor, said rotor connected to said impeller; and
   an axial displacement mechanism located proximal to and initiating axial movement of said impeller.

8. A diaphragm or flexible wall blood pump according to claim 7, in which an occluder blocks an inlet of the impeller of either side depending on its axial position.

9. A diaphragm or flexible wall blood pump according to claim 7, wherein said rotor is an integrated part of said impeller.

10. A diaphragm or flexible wall blood pump according to claim 7, wherein an axial shift of said rotor and said impeller is actuated by a driving electromagnetic field.

11. A diaphragm or flexible wall blood pump according to claim 7, wherein an axial shift of said rotor and said impeller and holding in position is done by the action of magnets.

12. A diaphragm or flexible wall blood pump according to claim 7, further comprising:
   a rotor bearing supporting said rotor and configured so said rotor and said impeller move in at least an axial direction.

13. A diaphragm or flexible wall blood pump comprising:
   a continuously running radial centrifugal hydraulic pump with an impeller having inlets on both sides;
   two diffusor elements arranged back to back and circumferentially surrounding said impeller, wherein each diffusor element is connected to and issues into separate blood pump housings;

a brushless electric motor mounted in fixed relationship to said blood pump housings and having a stator and a rotor, said rotor connected to said impeller; and an axial displacement mechanism located proximal to and initiating axial movement of said impeller.

14. A diaphragm or flexible wall blood pump according to claim 13, in which an occluder blocks an inlet of the impeller of either side depending on its axial position.

15. A diaphragm or flexible wall blood pump according to claim 13, wherein said rotor is an integrated part of said impeller.

16. A diaphragm or flexible wall blood pump according to claim 13, wherein an axial shift of said rotor and said impeller is actuated by a driving electromagnetic field.

17. A diaphragm or flexible wall blood pump according to claim 13, wherein an axial shift of said rotor and said impeller and holding in position is done by the action of magnets.

18. A diaphragm or flexible wall blood pump according to claim 13, further comprising:

a rotor bearing supporting said rotor and configured so said rotor and said impeller move in at least an axial direction.

* * * * *